Figure 1:
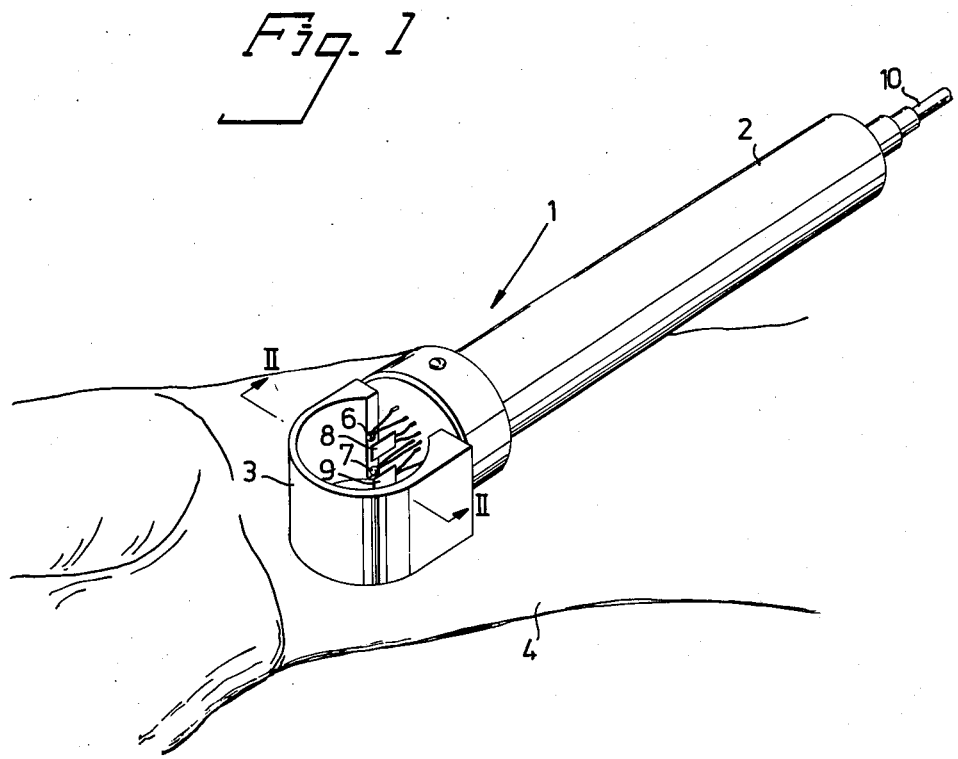

United States Patent [19]

Nilsson et al.

[11] 4,066,068

[45] Jan. 3, 1978

[54] METHOD AND APPARATUS FOR DETERMINING THE AMOUNT OF A SUBSTANCE EMITTED BY DIFFUSION FROM A SURFACE SUCH AS A DERM SURFACE

[75] Inventors: Gert Erik Nilsson; Åke Per Öberg, both of Linkoping, Sweden

[73] Assignee: Servo Med AB, Stockholm, Sweden

[21] Appl. No.: 635,348

[22] Filed: Nov. 26, 1975

[30] Foreign Application Priority Data

Nov. 28, 1974 Sweden .................................. 7414916

[51] Int. Cl.² ................................................ A61B 5/00
[52] U.S. Cl. ......................................... 128/2 R; 73/29; 128/2 H
[58] Field of Search ..................... 128/2 R, 2 H; 73/29

[56] References Cited

U.S. PATENT DOCUMENTS

| 3,139,085 | 6/1964 | Custance et al. ............. | 128/2 R |
|---|---|---|---|
| 3,318,302 | 5/1967 | Adams ........................... | 128/2 R |
| 3,886,797 | 6/1975 | Bauer ........................... | 73/29 X |
| 3,914,982 | 10/1975 | Zanetti ......................... | 73/29 |

Primary Examiner—Kyle L. Howell
Attorney, Agent, or Firm—Birch, Stewart, Kolasch & Birch

[57] ABSTRACT

A method and apparatus are provided for measuring quantitatively the amount of liquid and convection heat emitted from a surface by diffusion. When the surface is a derm surface the transepidermal water loss is measurable by a cylindrical shield device in which one open end is engaged with the derm layer and the other open end is exposed to the surroundings and within the cylindrical shield are placed a pair of temperature transducers and a pair of humidity transducers respectively positioned orthogonally to the derm surface at first and second known distances therefrom. The temperature and humidity readings at these two distances from the surface of the derm are processed by a circuit device to calculate the amount of water evaporated per surface unit over a given time interval.

10 Claims, 7 Drawing Figures

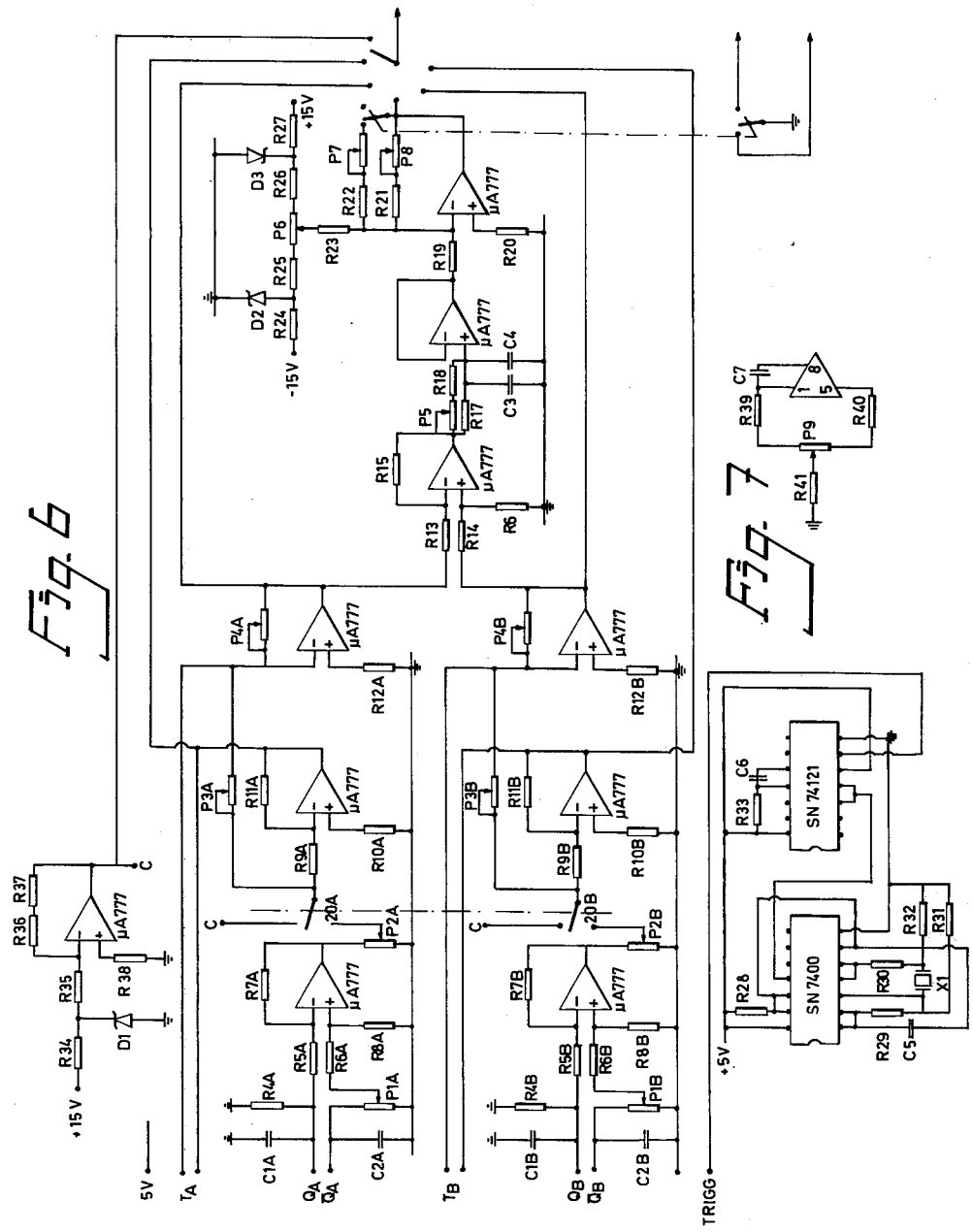

METHOD AND APPARATUS FOR DETERMINING THE AMOUNT OF A SUBSTANCE EMITTED BY DIFFUSION FROM A SURFACE SUCH AS A DERM SURFACE

This invention relates to a method and an apparatus intended to be used for quantitative determinations of the liquid amount and convection heat amount emitted from a surface by diffusion. The design of the invention also provides possibilities of simultaneously measuring the humidity, the saturation pressure of the water vapour and the partial pressure in question above said surface. The instrument is primarily intended for use for medical purposes.

Scientific studies of the anatomy, physiology and biochemistry of the derm have been described since a long time ago. Of particular interest has been the outermost layer, epidermis, of the derm which acts as a membrane semipermeable for water. The transepidermal water loss, T.E.W.L., is a stationary passive process, the speed of which depends on the humidity and temperature of the ambient air. The capacity of the entire organism of maintaining a constant inner environment, thus, depends on the efficient operation of said membrane. The knowledge of T.E.W.L. is of high prognostic value in cases of disturbed membrane function, which can occur, for example, with patients having skin burns or dermatologic diseases. Also from a pediatric aspect the knowledge of T.E.W.L. can be of great importance for a rapid judgment of suitable liquid treating measures during the period of development of a newborn child in the first ten days.

Earlier studies of local T.E.W.L. carried out in vivo have utilized either an aerated or non-aerated measuring capsule placed directly against the derm.

In the aerated measuring capsule the evaporation rate usually is determined in that air with a known water content is passed via feed and discharge plastic hoses through the measuring capsule. The water content of the outgoing air stream is measured, and T.E.W.L. can be calculated. Due to the fact that the transducers for relative humidity and temperature are not placed in the immediate vicinity of the measuring area, error sources difficult to control arise in the form of temperature drops in the feed conduits. Another method described in literature is based on the change in the heat conductivity of the humidity-carrying air stream at changing water content.

Into the non-aerated measuring capsule a water-absorbing substance, for example a hydroscopic salt, is placed and its weight is determined before and after the measuring operation. This method presupposes relatively long measuring periods and renders continuous measuring of T.E.W.L. impossible.

The aforesaid methods have in common that they, due to their complex nature, are primarily suitable for use in laboratories. The clinical evaluation of symptoms of dermatologic diseases and therapy effects, therefore, heretofore have been dependent to a large extent on the impressions received by the mind of the examining person at the inspection and palpation, although it would have been more desirable to base the judgment on more objective measures.

One object of the present invention is to provide a method and an apparatus for measuring T.E.W.L. which are so easy to handle that they can be applied in practical clinical work.

A further object of the present invention is to propose a measuring method and an apparatus with a short setting time, which render possible also continuous measurings of T.E.W.L.

Still a further object of the present invention has been to develop an instrument for measuring T.E.W.L. which permits free diffusion of the evaporated water to the ambient air and takes into consideration the local influence of the ambient air on the measuring area.

Another object of the present invention is to bring about an instrument with transducers for relative humidity and temperature disposed in the immediate vicinity of the measuring area in order to eliminate possible error sources.

The method and apparatus according to the invention also provide the possibility of determining the amount of certain substances other than water emitted from a surface. Furthermore, with minor changes also the heat amount emitted in the form of convection heat can be calculated.

According to the present invention an open measuring capsule is used to protect at least the immediate surrounding of a surface against passing outer gas streams. The measuring capsule is open both toward the surface and the surroundings, thereby permitting free diffusion of the substance emitted from the surface, and is designed so that a measuring area with a substantially stable diffusion zone within the measuring capsule is established. The surface may be the whole or a part of that surface, from which the amount of substance emitted by diffusion is to be determined. When measuring T.E.W.L., the surface, of course, is a portion of the patient's derm, and the substance is water.

An embodiment of the invention is based thereon that the evaporation from a water-emitting surface in the diffusion zone is approximately described by the equation (I).

$$\frac{1}{A} \frac{dm}{dt} = -D \frac{dp}{dx} \quad (I)$$

$A$ = area of the water-emitting surface (cm$^2$)
$m$ = mass of the evaporating water (mg)
$D$ = constant (0.887 mg/(cm · hours · mm Hg) at atmospheric pressure 760 mm Hg and air temperature 24° C)
$p$ = partial pressure of the water vapour (mm Hg)
$x$ = distance from the water-emitting surface (cm)

By determining the partial pressure gradient out from this surface, thus, the water amount evaporated per surface unit and time can be calculated. As the partial pressure gradient in the diffusion zone is independent of the distance from the water-emitting surface, said gradient can be calculated after the partial pressure of the water vapour has been determined in at least two points at different distances from the surface, preferably on a line orthogonal to the evaporating surface. The partial pressure in the two points is calculated from measuring values obtained from the simultaneous measuring of the relative humidity and the temperature.

Other embodiments of the invention are based thereon that the amount of other substances emitted from a surface by diffusion in a stable diffusion zone approximately can be described by equations anologous to equation I. These embodiments are based on the measuring of the relation between the partial pressure in question and the maximum partial pressure in the points at the temperature in question. Thereafter the partial pressure and the partial pressure gradient and the amount of emitted substance are calculated analogous to the calculation for water.

Figure 2:
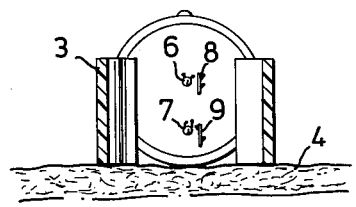
Figure 3:
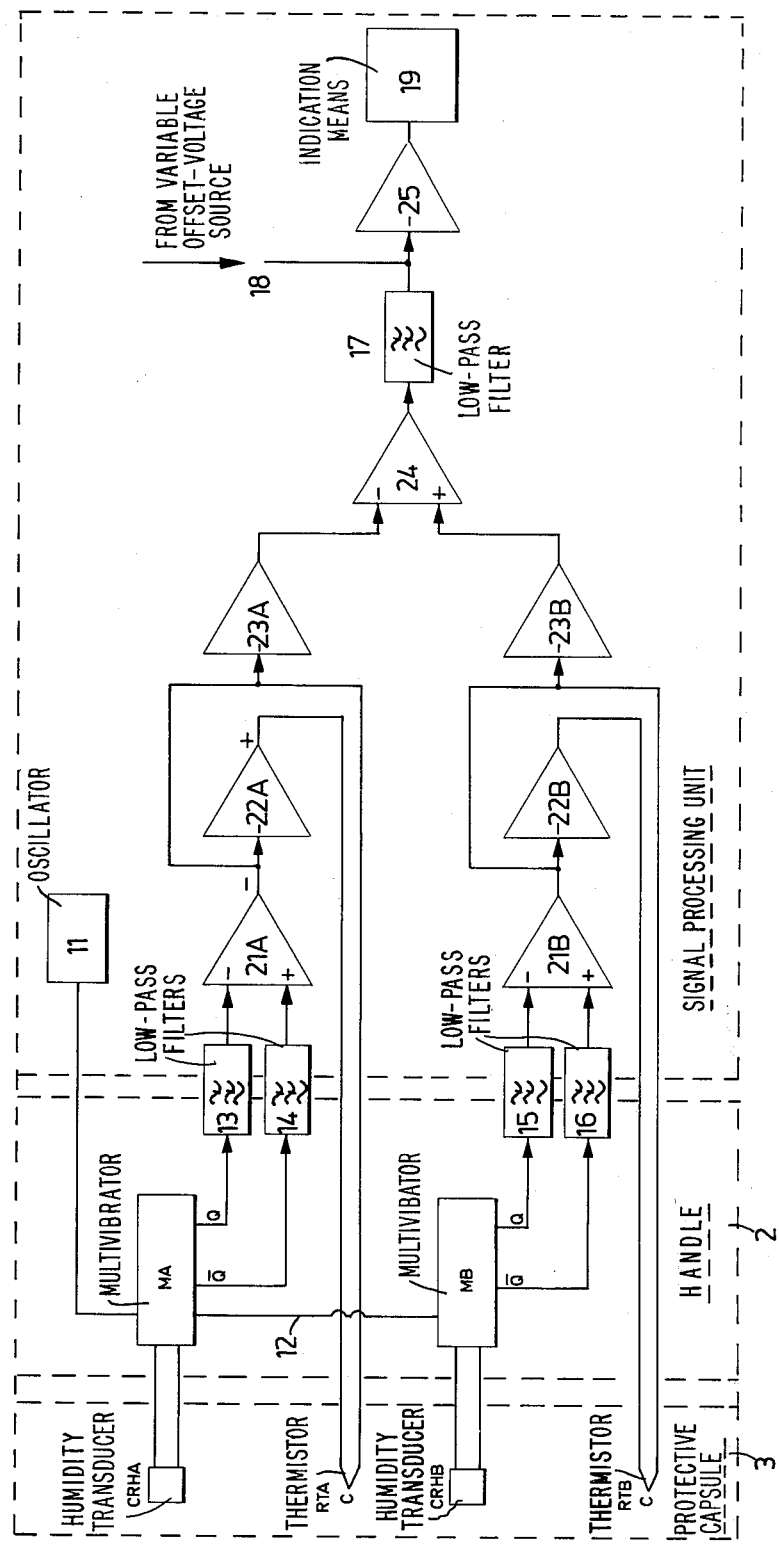
Figure 4:
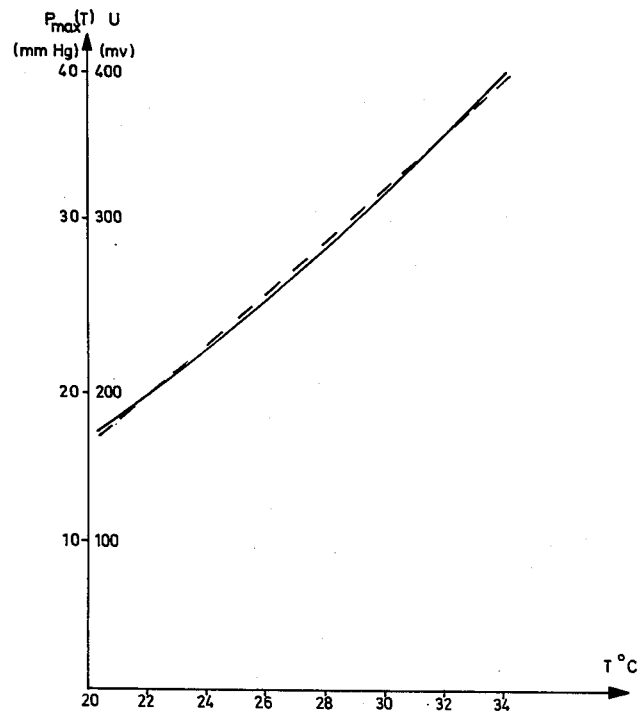

A preferred embodiment of the invention for use at the determination of T.E.W.L. is described with reference to the drawings, in which FIG. 1 in a perspective view shows the measuring body of an apparatus for determination of T.E.W.L., FIG. 2 is a section through the protective capsule of the measuring body, FIG. 3 shows a block diagram on the signal processing in an apparatus for determining T.E.W.L., FIG. 4 shows the transfer function of block 23A or 23B in FIG. 3, FIGS. 5-7 show circuit solutions according to the blocks in FIG. 3.

FIG. 1 shows the measuring body 1 of an apparatus for T.E.W.L. determination. The measuring body has a handle 2 of aluminium coated with plastic hose and a protective capsule 3 of teflon. The protective capsule is placed directly on the derm 4 of a patient's arm. As appears from FIGS. 1 and 2, the protective capsule is open both to the derm and the surroundings and so designed, that it defines together with the derm an upwardly open space 5 of substantially cylindric shape. Due to the design and location of the capsule, at least the portion of said space which is located closest to the derm is at least partially protected against air streams or the like flowing past the patent's arm. In said space, therefore, a measuring area with a substantially stable diffusion zone is created.

FIG. 2 is a section through the protective capsule of the measuring body. Within said protective capsule two sensing members 6, 7 for the temperatures and two sensing members 8, 9 for the relative humidity are provided. The temperature sensing members are thermistors RTA, RTB, and the members for sensing the relative humidity are capacitive transducers CRHA, CRHB of thin-film type, the capacitance of which varies substantially according to the equation $$C = C_o + kRH \tag{II}$$

$C$ = total capacitance of the transducer
$C_o$ = basic capacitance of the transducer
$k$ = constant
$Rh$ = relative humidity.

The transducers for the relative humidity, as appears from FIGS. 1 and 2, are so disposed in the protective capsule that each scans the relative humidity in its area of a plane perpendicular to the derm, which areas lie at different distances from the derm. The thermistors are so disposed in the protective capsule that they scan the temperature in two points on a line orthogonal to the derm 4, which points substantially are located at the same distance from the derm as the centers of said areas.

Several variants of the measuring body shown in FIGS. 1 and 2 can be imagined within the scope of the invention. Neither the handle 2 nor the protective capsule 3 must be designed according to FIGS. 1-2, but the main feature is that the protective capsule 3 at least partially protects a measuring area adjacent the derm against streams of air or other gases, which otherwise would pass the derm and the measuring area, and thereby a stable diffusion zone is created where the scanning members can be disposed. Furthermore, the number of thermistors and capacitive transducers may exceed two, and they must not necessarily be oriented along planes and lines orthogonal to the derm.

The measuring body shown in FIG. 1 is connected by a cable 10 containing a plurality of insulated conductors to a unit (not shown) for processing signals, which are transmitted via said conductors, and for indication of T.E.W.L. and possible other magnitudes, such as temperature etc.

FIG. 3 shows a block diagram for processing the signals from the sensing members to the indication means. The block diagram is divided by dashed lines into three areas in order to inform where in the apparatus the different parts of the block diagram are located. The left-hand area 3 comprises the parts located in the protective capsule of the measuring body. The central area 2 comprises the parts located in the handle of the measuring body. The right-hand area, without designation, comprises the parts located in the signal processing unit.

The sensing members for the temperature are designated in FIG. 3 by RTA and, respectively, RTB, and the members for sensing the relative humidity are designated by CRHA and, respectively, CRHB. CRHA and CRHB are included as elements determining the pulse duration each in a monostable multivibrator MA and, respectively, MB. The multivibrator MA is triggered by clock pulses with the frequencey 1 MHz from the oscillator 11. Upon return of the multivibrator MA to its neutral position, the rocker MB is triggered via the connection 12. By this mode of operation the pulse durations of the two monostable multivibrators are prevented from influencing each other. The outsignals from the two monostable multivibrator are filtered in low-pass filters 13, 14, 15 and 16 and are thereby transformed to direct voltages substantially proportional to the surface of the pulses. The information-carrying filtered signals from the outputs of the monostable multivibrator Q and, respectively, Q are thereafter pressed on the differential - connected input amplifier 21A and, respectively, 21B in the channel in question. By means of a variable voltage division (not shown) of the filtered signal from the respective Q-output, the respective input step can be so calibrated that the out-signal from this step is zero when the relative humidity is zero. The sensitivity in the amplification of the input step is calibrated with a voltage division (not shown) of the out-signal from this step. Said out-signal, thus, is a direct voltage proportional to the relative humidity. The signal can be taken out from the subsequent amplifier 22A and, respectively, 22B. These amplifier steps serve only as sign-changers for the signals.

The sign-changed signals from the amplifier steps 22A and, respectively, 22B are supplied to the amplifier steps 23A and, respectively, 23B via the thermistors, while the signals with unchanged signs from the amplifier steps 21A and, respectively, 21B are directly supplied to the amplifier steps 23A and, respectively, 23B. By this arrangement the amplifier steps 23A and 23B in combination with the thermistors RTA and RTB are given a transfer function depending on the sensed temperatures according to the dashed line in FIG. 4. Said transfer function should as closely as possible agree with the maximum partial pressure of the water vapour according to the solid line in FIG. 4, in order to render the out-signals from the amplifier steps 23A and, respectively, 23B as closely as possible proportional to the partial pressure of the water vapour at CRHA and, respectively, CRHB.

The difference between the partial pressures at CRHA and CRHB is calculated in the amplifier step 24 to which the out-signals from the amplifier steps 23A and 23B are supplied. This difference in partial pressure is proportional to the partial pressure gradient in the measuring area in the protective capsule. A low-pass filter 17 filters off possible rapid fluctuations in the out-signal from the amplifier step 24 which are due to circulating air streams in the measuring capsule. This provides a more stable signal, which is more suitable for reading with digital display. The last amplifier step 25 provides the possibility of rapid calibration of the instrument by the supply of a variable offset-voltage via the conductor 18. The output on the amplifier step is coupled to an indication means 19, which digitally indicates the size of the out-signal of the amplifier step.

It is in principle also possible, with minor changes of the method and apparatus according to the invention, to measure emitted convection heat, which is described by the equation $$\frac{1}{A} \frac{dQ}{dt} = -\lambda \frac{\delta T}{\delta x} \qquad (III)$$

$A$ = area of heat emitting surface (m²)
$Q$ = emitted heat amount (Wattseconds)
$\lambda$ = constant (0.024 Watt/meter · degree at T = 0° C)
$T$ = temperature (° C)
$x$ = distance from heat emitting surface (m)

Figure 5:
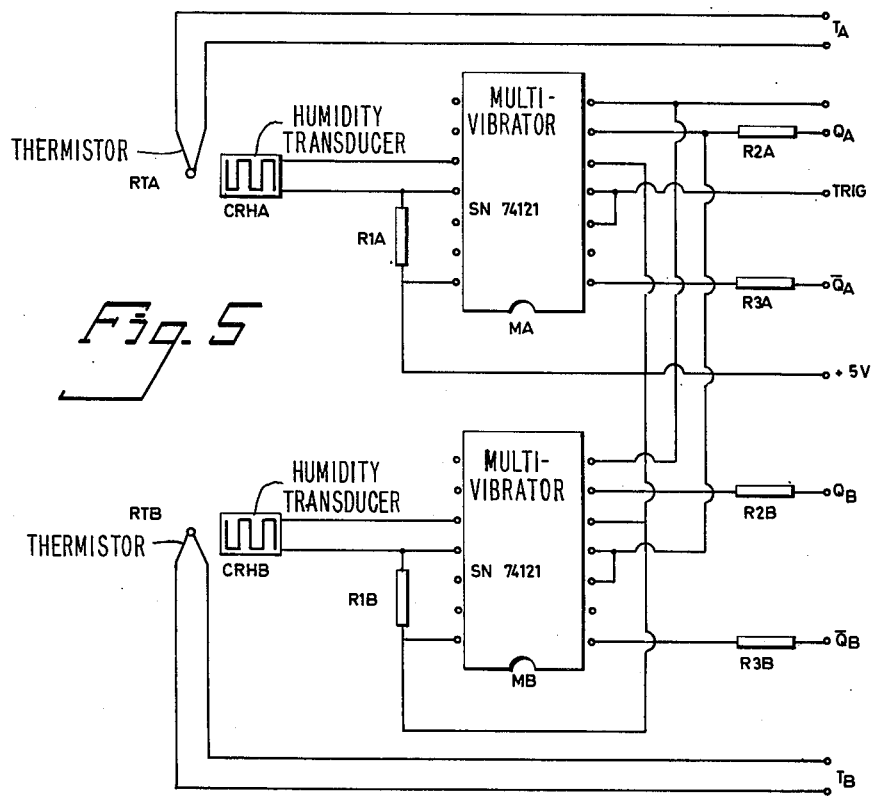

This is possible if the humidity-responsive signals from the input amplifiers are replaced by fixed voltages. The instrument then acts as an instrument which purely measures the temperature difference, and the emitted convection heat amount can be calculated according to equation III. A circuit diagram over such an embodiment of the invention is shown in FIGS. 5–6 where the switches 20A and 20B are used for switch-over between measuring the evaporation amount and the convection heat amount. FIG. 7 shows offset compensation according to this embodiment. As base values for components adapted for use in an apparatus according to FIGS. 5–7 the following component data can be mentioned where k stands for kiloohm:

R 1A = R 1B = 8,2 k 1%
R 2A = R 2B = R 3A = R 3B = 1 k
R 4A = R 4B = 47 k
R 5A = R 5B = R 6A = R 6B = R 7A = R 7B = R 8A = R 8B = 100 k
R 9A = R 9B = 100 k 1%
R 10A = R 10B = 47 k
R 11A = R 11B = 100 k 1%
R 12A = R 12B = 6,8 k
R 13 = R 14 = R 15 = R 16 = 100 k 1%
R 17 = 68 k
R 18 = 1 k
R 19 = 10 k
R 20 = 6,8 k
R 21 = 68 k
R 22 = 6,8 k
R 23 = 1000 k
R 24 = R 27 = 4,7 k R 25 = R 26 = 1 k
R 28 = 1 k
R 29 = 1 k
R 30 = 2,2 k
R 31 = 2,2 k
R 32 = 2,2 k
R 33 = 1 k
R 34 = 6,8 k
R 35 = 100 k 1%
R 36 = 6,8 k
R 37 = 0,1 k
R 38 = 2 k
R 39 = R 40 = 1800 k
R 41 = 4700 k $P_{1A} = P_{1B}$ = 50 k
$P_2A = P_{2B}$ = 0,5 k
$P_{3A} = P_{3B}$ = 20 k
$P_{4A} = P_{4B}$ = 50 k
$P_5$ = 200 k
$P_6$ = 1 k
$P_7$ = 5 k
$P_8$ = 50 k
$P 9$ = 2000 k

C 1A = C 1B = C 2A = C 2B = 4,7 nF
C 3 = C 4 = 220 μF 10V bipolar
C 5 = 0,1 μF
C 6 = 68 pF
C 7 = 33 pF CRHA = CRHB = humidity transducer type Vaisala HMP-11
RTA = RTB = thermistor M81
D 1 = D 2 = D 3 = 4,7V Zener diodes
X 1 = crystal 1 MHz SN 7400 and SN 74121 are integrated circuits of the make Texas Instruments, and μA 777 are integrated circuits of the make Fairchild.

The method and apparatus according to the invention have been described above in connection with the measuring of evaporated water. The invention, however, can be applied also to other substances where the equation I is applicable and where transducers are provided for measuring the relation between a partial pressure in question and the maximum partial pressure at the temperature in question. In such cases, of course, the transfer function of block 23A or 23B in FIG. 3 can have an appearance other than that shown in FIG. 4.

Further variants and modifications of the described embodiments of methods and apparatuses according to the invention are, of course, imaginable within the scope of the claims.

We claim:
1. A method at the determination of the amount of a substance emitted by diffusion from a surface, comprising the steps of creating a substantially stable diffusion zone with a measuring area by protecting at least the immediate surroundings of the entire surface or a part thereof against outer passing gas streams, sensing the temperature and the relation between the absolute partial vapor pressure and the saturation pressure at the temperature in question substantially simultaneously each in at least two points within the measuring area at different distances from the surface, determining the absolute partial vapor pressure in at least two points within the measuring area at different distances from the surface with the help of the results of said sensing, and estimating the partial pressure gradient in the diffusion zone with the help of said partial pressure.

2. A method according to claim 1 at which a substantially cylindrical area is protected.

3. A method for the determination of transepidermal water loss emitted by diffusion from a derm surface comprising the steps of creating a substantially stable diffusion zone with a substantially cylindrical measuring area by protecting at least the immediate surroundings of the entire surface or a part thereof against outer passing gas streams, sensing the temperature and the relation between the absolute partial vapor pressure and the saturation pressure at the temperature in question substantially simultaneously each in at least two points within the measuring area at different distances from the surface, determining the absolute partial vapor pressure in at least two points within the measuring area at different distances from the surface with the help of the results of said sensing and estimating the partial pressure gradient in the diffusion zone with the help of said partial pressure;

said two points at which said temperature is sensed comprising at first and second points located on or in the vicinity of a first line substantially orthogonal to said derm, and the respective distances the said two points from the derm at which said absolute partial pressure is determined substantially agree with the respective distances of the said first and second points from said derm.

4. An apparatus for determining the amount of a substance emitted by diffusion from a surface, comprising an open measuring capsule designed so as to at least partially protect at least the immediate surrounding of the entire surface or a part thereof against outer passing gas streams, sensing members in the protective capsule to sense the temperature and the relation between the absolute partial pressure and the saturation pressure at the temperature in question for the substance substantially simultaneously each in at least two points at different distances from the surface in its protected surrounding, first means to process information on sensed magnitudes from the sensing members and producing signals representing the absolute partial pressure of the substance in at least two of said points, and second means to produce from said signals a magnitude representing the partial pressure gradient of the substance within said protected surrounding.

5. An apparatus according to claim 4 where the protective capsule and the surface together define an open space of substantially cylindrical shape.

6. An apparatus according to claim 4 for determining transepidermal water loss in which said surface is a derm and, in which the sensing means comprise two temperature transducers adapted to sense the temperature at two first points located on or in the vicinity of a first line substantially orthogonal to the derm, two humidity transducers adapted to sense the relative humidity at two second points located on or in the vicinity of a second line also orthogonal to the derm, the respective distances of said two second points from the derm substantially agreeing with the respective distances of said two first points from the derm.

7. An apparatus according to claim 6 wherein the temperature transducers comprise two thermistors, and the humidity transducers comprise two capacitive transducers of thin-film type, the capacitance of which varies at least substantially linearly with the relative humidity.

8. A method for the determination of the amount of a substance emitted by diffusion from a derm surface for diagnostic purposes, comprising the steps of creating a substantially stable diffusion zone with a measuring area by protecting at least the immediate surroundings of the entire surface or a part thereof against outer passing gas streams, sensing the temperature and the relation between the absolute partial pressure and the saturation pressure at the temperature in question for the substance substantially simultaneously each in at least two points within the measuring area at different distances from the surface, determining the absolute partial pressure of the substance in at least two points within the measuring area at different distances from the surface with the help of the results of said sensing, and estimating the partial pressure gradient in the diffusion zone with the help of said partial pressure.

9. A method according to claim 8 at which a substantially cylindrical area is protected.

10. The invention defined in claim 9, wherein said partial pressure at each of said points is determined as a function of temperature and relative humidity by sensing the value of temperature at first and second points substantially on a first line orthogonal to said derm;

sensing the value of relative humidity at first and second points respectively adjacent said two first points substantially on a second line orthogonal to said derm;

said first and second points on both said first and second lines being respectively equidistant from said derm; and calculating said partial pressure at each said point from said sensed values.

* * * * *